(12) United States Patent
Farwick et al.

(10) Patent No.: US 9,456,973 B2
(45) Date of Patent: Oct. 4, 2016

(54) METHIONYL-METHIONINE STEREOISOMERS AND USE THEREOF IN COSMETICS

(71) Applicants: Mike Farwick, Essen (DE); Matthias Mentel, Dortmund (DE); Ursula Maczkiewitz, Essen (DE); Andreas Seifert, Bottrop (DE)

(72) Inventors: Mike Farwick, Essen (DE); Matthias Mentel, Dortmund (DE); Ursula Maczkiewitz, Essen (DE); Andreas Seifert, Bottrop (DE)

(73) Assignee: EVONIK DEGUSSA GMBH, Essen (DE)

(*) Notice: Subject to any disclaimer, the term of this patent is extended or adjusted under 35 U.S.C. 154(b) by 2 days.

(21) Appl. No.: 14/453,161

(22) Filed: Aug. 6, 2014

(65) Prior Publication Data

US 2015/0044158 A1 Feb. 12, 2015

(30) Foreign Application Priority Data

Aug. 6, 2013 (DE) ......................... 10 2013 215 434

(51) Int. Cl.
| | | |
|---|---|---|
| *A61K 8/64* | (2006.01) | |
| *A61Q 3/00* | (2006.01) | |
| *A61Q 5/12* | (2006.01) | |

(52) U.S. Cl.
CPC . *A61K 8/64* (2013.01); *A61Q 3/00* (2013.01); *A61Q 5/12* (2013.01)

(58) Field of Classification Search
None
See application file for complete search history.

(56) References Cited

U.S. PATENT DOCUMENTS

| | | |
|---|---|---|
| 7,858,580 B2 | 12/2010 | Lersch et al. |
| 2007/0003509 A1 | 1/2007 | Farwick et al. |
| 2008/0249073 A1 | 10/2008 | Farwick et al. |
| 2010/0098801 A1 | 4/2010 | Kobler et al. |
| 2010/0158847 A1* | 6/2010 | Fahnestock ............ A61K 8/64 424/70.6 |
| 2010/0311668 A1 | 12/2010 | Farwick et al. |
| 2012/0024409 A1 | 2/2012 | Kunzmann |
| 2012/0070394 A1* | 3/2012 | Seguin .................... A61K 8/64 424/62 |
| 2013/0008384 A1 | 1/2013 | Kobler et al. |
| 2013/0011514 A1 | 1/2013 | Kobler et al. |

FOREIGN PATENT DOCUMENTS

| | | |
|---|---|---|
| DE | 102008001788 | 11/2009 |
| DE | 102008042932 A1 | 4/2010 |
| JP | 2999301 | 11/1999 |
| WO | WO0051556 | 9/2000 |
| WO | WO2007068401 | 6/2007 |
| WO | WO 2010/043558 A1 | 4/2010 |

OTHER PUBLICATIONS

Betts et al., "Amino acid properties and consequences of substitutions", Bioinformatics for Geneticists, Chptr. 14, pp. 290-316, Publ. John Wiley and Sons, Ltd. (2003).*
L-methionyl-L-methionine, chemical structure 5361185, pp. 1-2, accessed Mar. 29, 2016 at URL chemspider.com/Chemical-Structure.5361185.html.*
European Search Report dated Dec. 8, 2014 received in a corresponding foreign application.
Schrader, K. et al., "Grundlagen and Rezepturen der Kosmetika" ["Principles and Formulations of Cosmetics"], 1989, 2nd edition, p. 329 to 341, Hüthig Buch Verlag Heidelberg.

* cited by examiner

*Primary Examiner* — Julie Ha
*Assistant Examiner* — Kristina M Hellman
(74) *Attorney, Agent, or Firm* — Scully, Scott, Murphy & Presser, P.C.

(57) ABSTRACT

The present invention relates to a cosmetic formulation comprising certain methionyl-methionine stereoisomers and to the use of methionyl-methionine for nail and/or hair treatment.

6 Claims, 12 Drawing Sheets

METHIONYL-METHIONINE STEREOISOMERS AND USE THEREOF IN COSMETICS

FIELD OF THE INVENTION

The present invention relates to cosmetic formulations comprising certain methionyl-methionine stereoisomers and to the use of methionyl-methionine for nail and/or hair treatment.

PRIOR ART

Methionine is a customary active ingredient for improving the properties of hair. Thus, the use of haircare compositions comprising methionine for improving the strength and the condition of the hair is described, for example, in WO00/51556.

The cosmetic use of dipeptides comprising at least one methionine of the formula XM or MX, in particular L-methionyl-L-methionine, for lightening skin is described in JP2999301.

The production and the use of stereoisomeric mixtures of methionyl-methionine and its salts as a feed additive for fish and crustaceans is described in WO2010/043558. Preferably the described dipeptide is present in the feed mixture as DD/LL/LD/DL mixture, as DL/LD or DD/LL mixture, and in a particularly preferred use the dipeptide is present as enantiomer pair D-methionyl-L-methionine and L-methionyl-D-methionine.

Despite the above, there is a need for providing a substitute for methionine in cosmetic applications.

SUMMARY OF THE INVENTION

Surprisingly, it has been found that the cosmetic formulations, described below, comprising certain methionyl-methionine stereoisomers can be used as a suitable substitute for methionine in cosmetic applications.

Surprisingly and unexpectedly, it has been found that these stereoisomers have excellent and very broad application properties. These properties overshadow those of L-methionine in certain applications. Moreover, in hair-specific application technology, they surpass the properties of other customary market products such as e.g. of hydrolysed wheat proteins.

The present invention therefore provides a cosmetic formulation comprising certain methionyl-methionine stereoisomers.

The invention further provides the use of methionyl-methionine for nail and/or hair treatment.

It is an advantage of the present invention that the methionyl-methionine stereoisomers have a low cytotoxicity.

It is a further advantage of the present invention that the methionyl-methionine stereoisomers have good stability in aqueous solution.

A further advantage of the present invention is that methionyl-methionine stereoisomers have a relatively low odour.

Another advantage of the present invention is that the methionyl-methionine is both able to improve properties such as combability, softness, volume, shapeability, handleability, detangleability of undamaged and damaged hair, as well as impart a beautiful shine to the hair.

For the dipeptide methionyl-methionine of general formula (I)

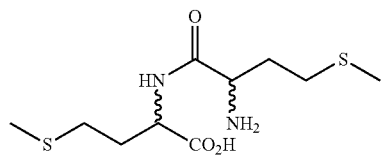

general formula (I)

there are four different stereoisomers: D-methionyl-L-methionine, L-methionyl-D-methionine, L-methionyl-L-methionine and D-methionyl-D-methionine:

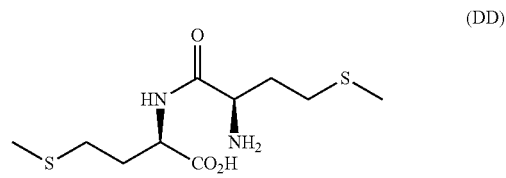

(DD)

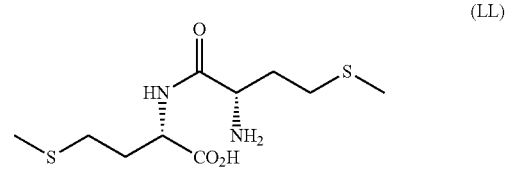

(LL)

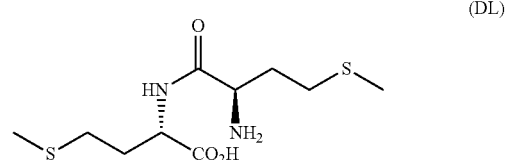

(DL)

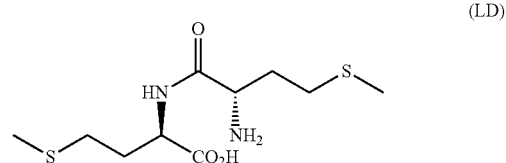

(LD)

Here, DD and LL behave amongst themselves as image and mirror-image, i.e. they are enantiomers and therefore also have the same physical properties. The same is true for the pair DL and LD.

By contrast, the two pairs DD/LL and DL/LD are diastereomeric relative to one another, i.e., they have different physical data. Thus, at room temperature, for example the enantiomer pair DD/LL has a solubility of 21 g/L in water, whereas the solubility of the enantiomer pair DL/LD is 0.4 g/L.

The present invention therefore provides a cosmetic formulation comprising at least one methionyl-methionine stereoisomer selected from the group D-methionyl-L-methionine, L-methionyl-D-methionine and D-methionyl-D-methionine.

DETAILED DESCRIPTION OF THE INVENTION

Figure 1:
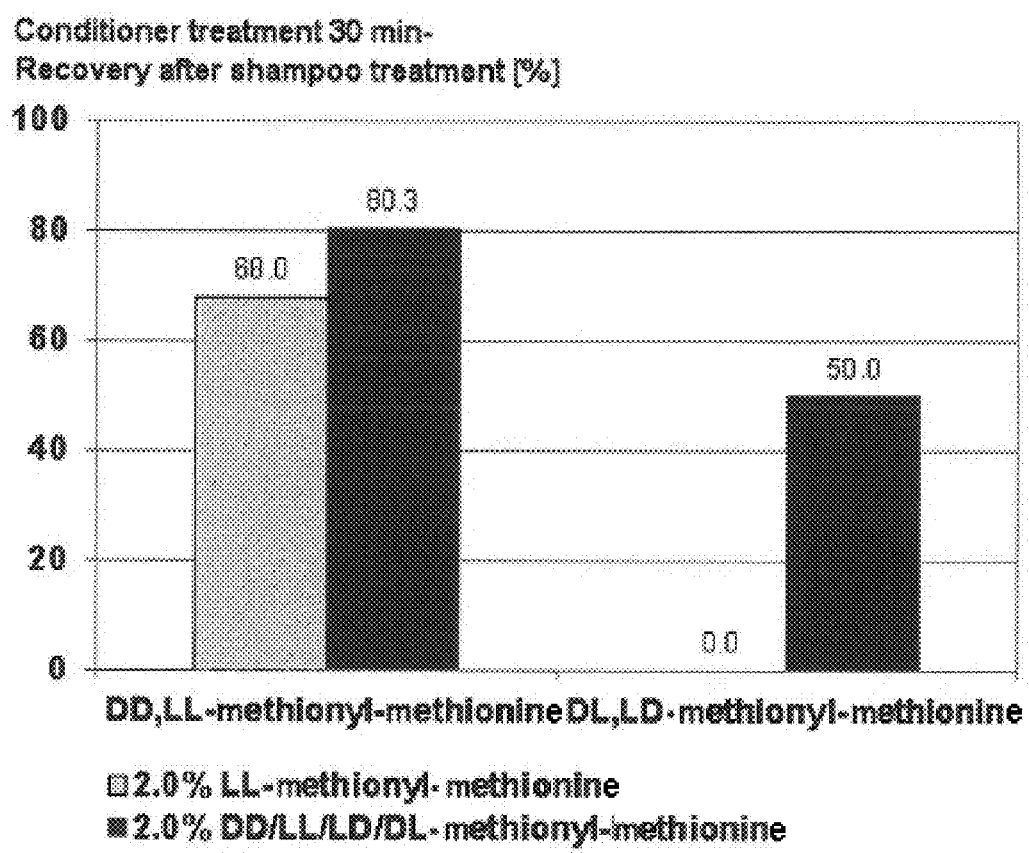
FIG. 1 is a graph illustrating the ability of methionyl-methionine stereoisomers to be washed out after conditioning treatment over 30 minutes as described in the examples of the present invention.

In connection with the present invention, the term "D-methionyl-L-methionine" has the same meaning as "DL-methionyl-methionine". The same is true for L-methionyl-D-methionine, L-methionyl-L-methionine and D-methionyl-D-methionine.

The use according to the present invention, where it is the case of a use on a living species, is exclusively a cosmetic and a non-therapeutic use.

Unless stated otherwise, all of the stated percentages (%) are percent by mass.

Preferably, in the formulation according to the present invention, all methionyl-methionine stereoisomers selected from the group D-methionyl-L-methionine, L-methionyl-D-methionine and D-methionyl-D-methionine are present.

It can be advantageous according to the present invention if the formulation additionally comprises L-methionyl-L-methionine, because for example the presence of L-methionyl-L-methionine is required by the production process of the stereoisomers.

Preferably, in the formulation according to the present invention, all methionyl-methionine stereoisomers selected from the group D-methionyl-L-methionine, L-methionyl-D-methionine, L-methionyl-L-methionine and D-methionyl-D-methionine are thus present.

Preferably, the total amount of L-methionyl-L-methionine based on the total weight of all methionyl-methionine stereoisomers present in the formulation according to the present invention is less than or equal to 50% by weight, preferably less than 35% by weight, particularly preferably less than 20% by weight.

Formulations preferred according to the present invention have a weight ratio of DL- and LD-methionyl-methionine to DD- and LL-methionyl-methionine of 9:1 to 2:3, preferably 8:2 to 1:1, in particular 7:3 to 3:2, where per enantiomer pair in each case the sum of the individual enantiomers is taken into consideration. The aforementioned formulation does not exclude the possibility of only one of the enantiomers of an enantiomer pair being present in the formulation.

In an alternative preferred use, DL- and LD-methionyl-methionine to DD- and LL-methionyl-methionine is in the ratio 10:90-0.01:99.99.

The formulations according to the present invention can comprise for example at least one additional component selected from the group of emollients,
emulsifiers,
thickeners/viscosity regulators/stabilizers,
UV light protection filters,
antioxidants,
hydrotropes (or polyols),
solids and fillers,
film formers,
pearlescence additives,
deodorant and antiperspirant active ingredients,
insect repellents,
self-tanning agents,
preservatives,
conditioners,
perfumes,
dyes,
odour absorbers,
cosmetic active ingredients,
care additives,
superfatting agents,
solvents.

Substances which can be used as exemplary representatives of the individual groups are known to a person skilled in the art and can be found, for example, in the German application DE 102008001788.4. This patent application is herewith incorporated as reference and thus forms part of the disclosure.

As regards further optional components and the amounts of these components used, reference is made expressly to the relevant handbooks known to a person skilled in the art, e.g., K. Schrader, "Grundlagen and Rezepturen der Kosmetika [Fundamentals and Formulations of Cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

The present invention further provides the use of methionyl-methionine for treating nails and/or hair, in particular hair, for conditioning hair, for increasing the shine of the hair, for increasing the tensile strength of the hair, for increasing the volume of hair, for increasing the colour intensity of the hair, for increasing the loadability of hair, for protecting the hair against UV damage, for protecting the hair against oxidative damage, for protecting the hair against thermal damage, for protecting the hair against chemical damage, such as for example by alkaline treatment or by treatment with reducing agents, and/or for improving the mechanical properties of nails.

Preferably, at least one methionyl-methionine stereoisomer selected from the group D-methionyl-L-methionine, L-methionyl-D-methionine and D-methionyl-D-methionine is used according to the present invention.

According to the present invention, in particular the aforementioned formulations can be used, with formulations preferred according to the present invention being preferably used according to the invention.

The examples listed below describe the present invention by way of example, without any intention of restricting the invention, the scope of application of which is apparent from the entirety of the description and the claims, to the embodiments specified in the examples.

The following figures are a component of the examples:

FIG. 1. Ability of methionyl-methionine stereoisomers to be washed out after conditioning treatment over 30 minutes.

Figure 2:
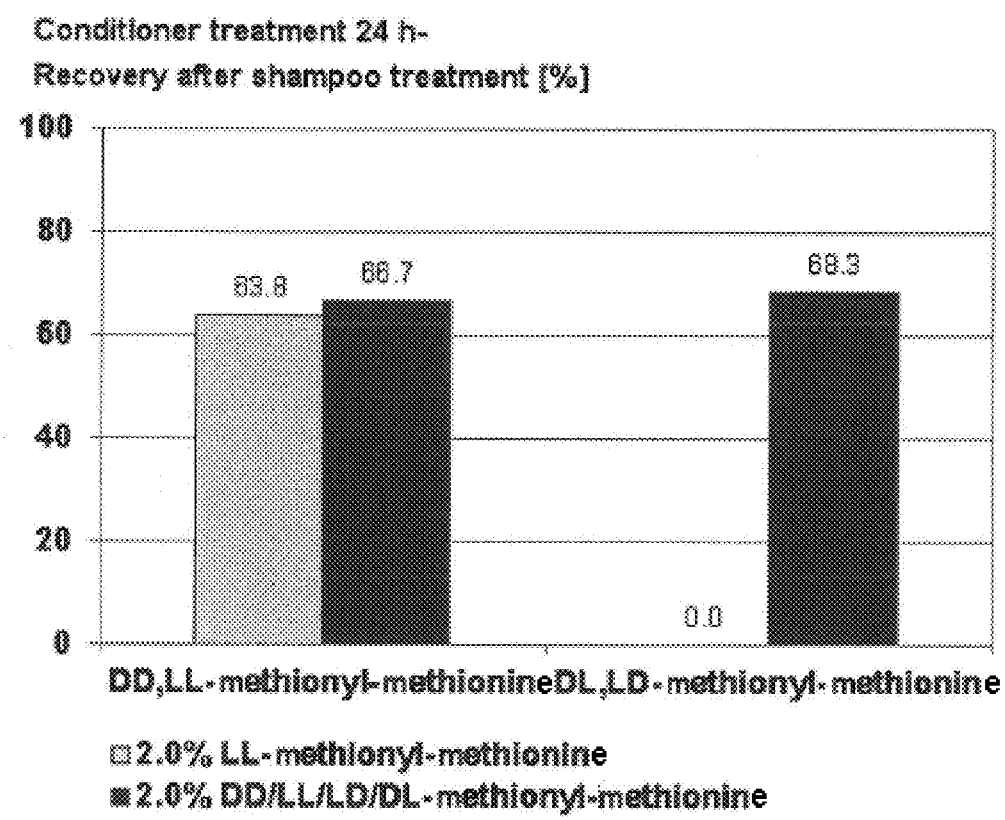
FIG. 2 is a graph illustrating the ability of methionyl-methionine stereoisomers to be washed out after conditioning treatment over 24 hours as described in the examples of the present invention.

FIG. 2. Ability of methionyl-methionine stereoisomers to be washed out after conditioning treatment over 24 hours.

Figure 3:
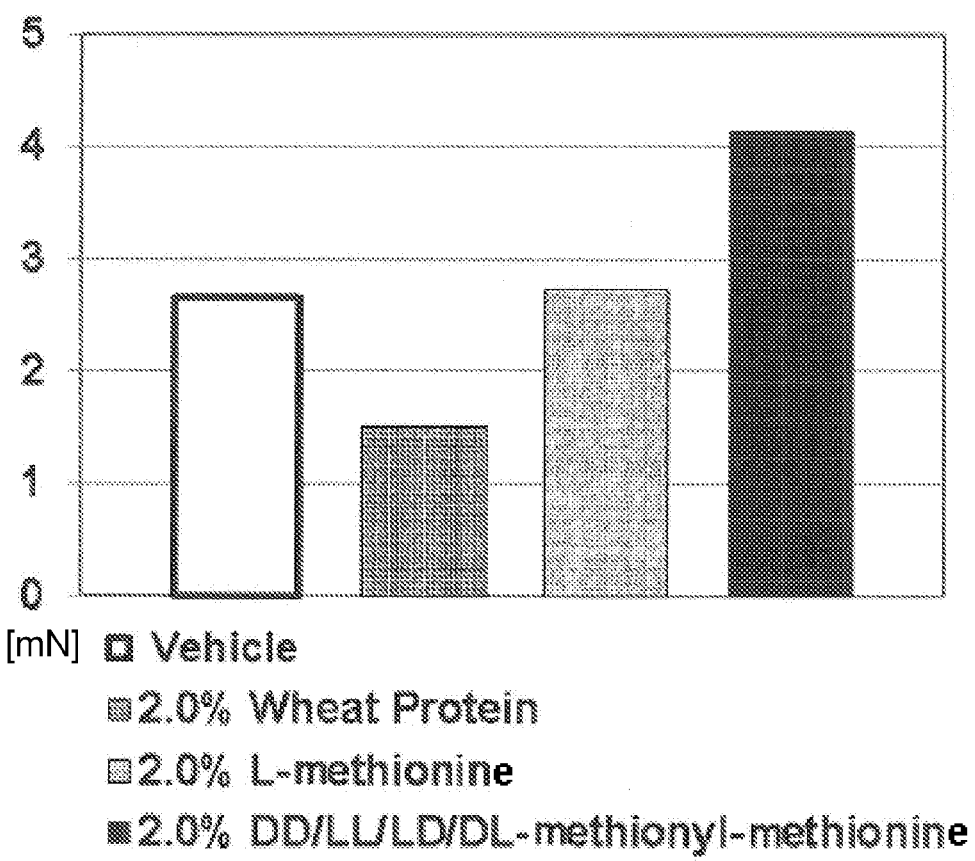
FIG. 3 is a graph illustrating the repair of bleached hair as described in the examples of the present invention.

FIG. 3. Repair of bleached hair. The improvements after hair treatment with a simple hair conditioner (Table 3) of the parameter Load determined by means of a Tensile Tester at 15% elongation are shown. Values shown are in millinewtons (mN).

Figure 4:
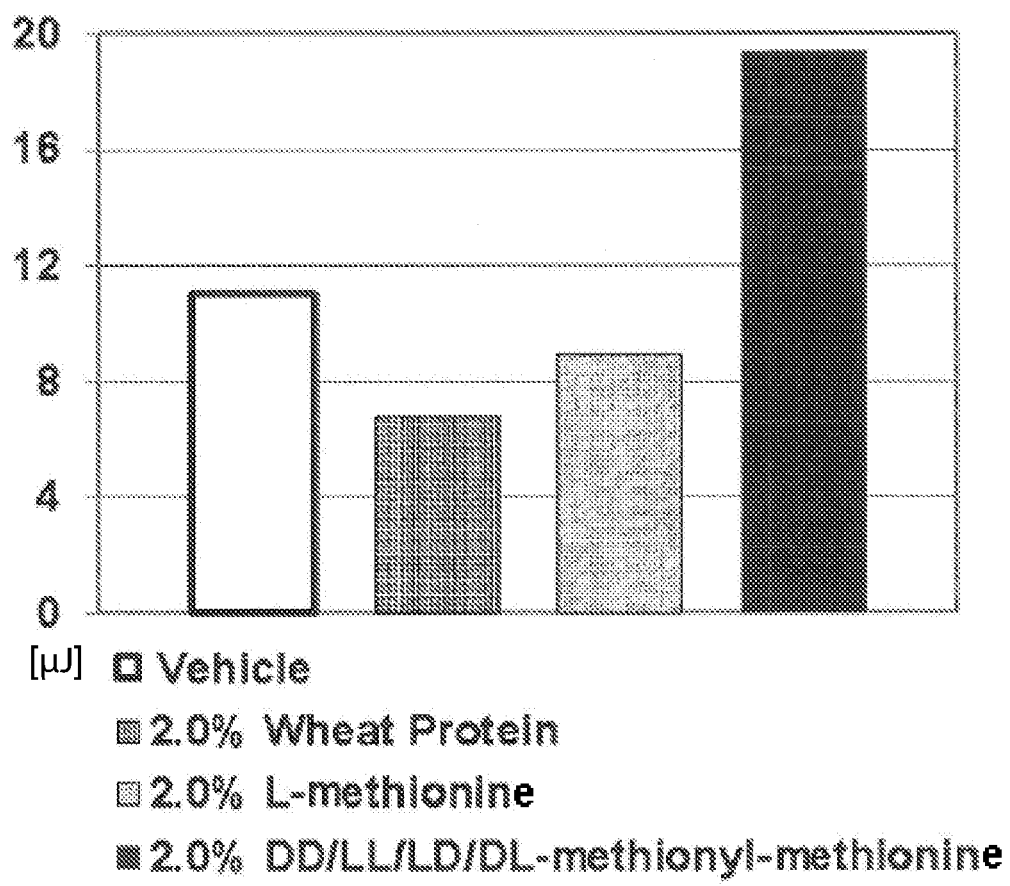
FIG. 4 is a graph illustrating the repair of bleached hair as described in the examples of the present invention.

FIG. 4: Repair of bleached hair. The improvements after hair treatment with a simple hair conditioner (Table 3) of the parameter Work determined by means of a Tensile Tester up to 15% elongation are shown. Values shown are in microjoules (µJ).

Figure 5:
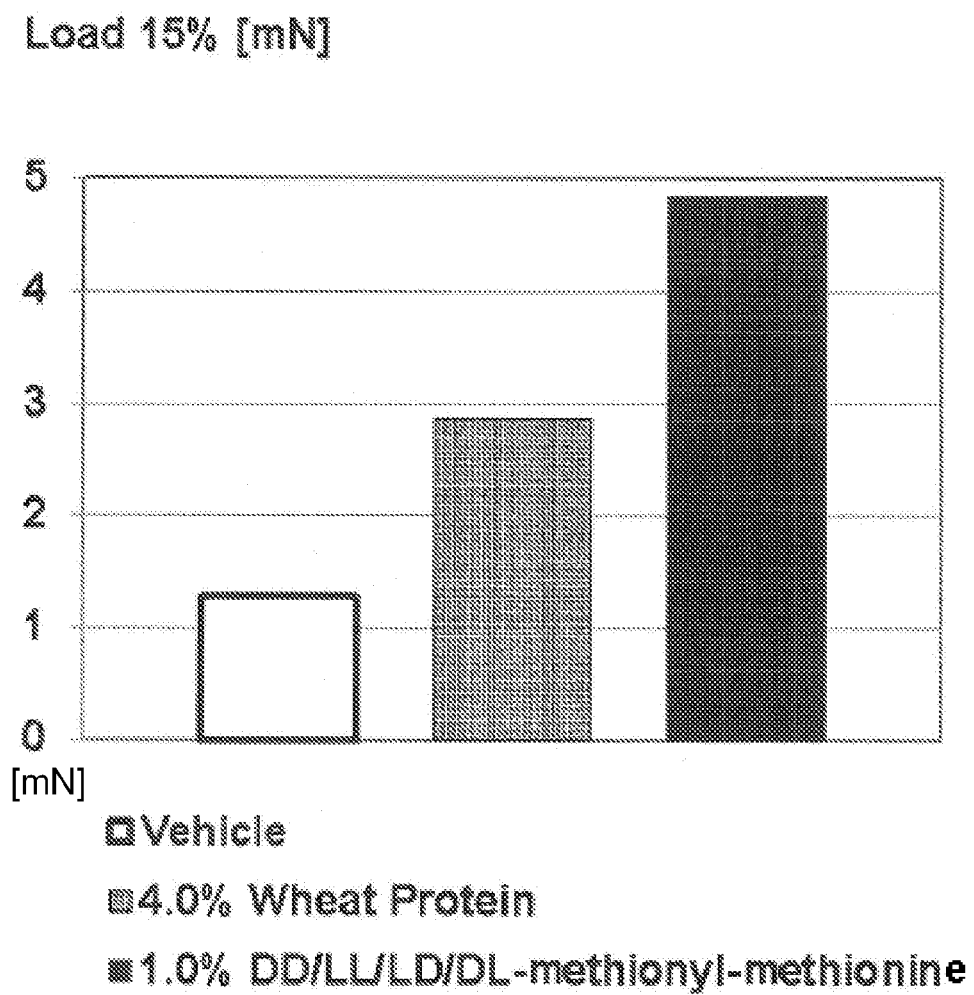
FIG. 5 is a graph illustrating the repair of bleached hair as described in the examples of the present invention.

FIG. 5: Repair of bleached hair. The improvements after hair treatment with an expanded hair conditioner (Table 4) of the parameter Load determined by means of a Tensile Tester at 15% elongation are shown. Values shown are in millinewtons (mN).

Figure 6:
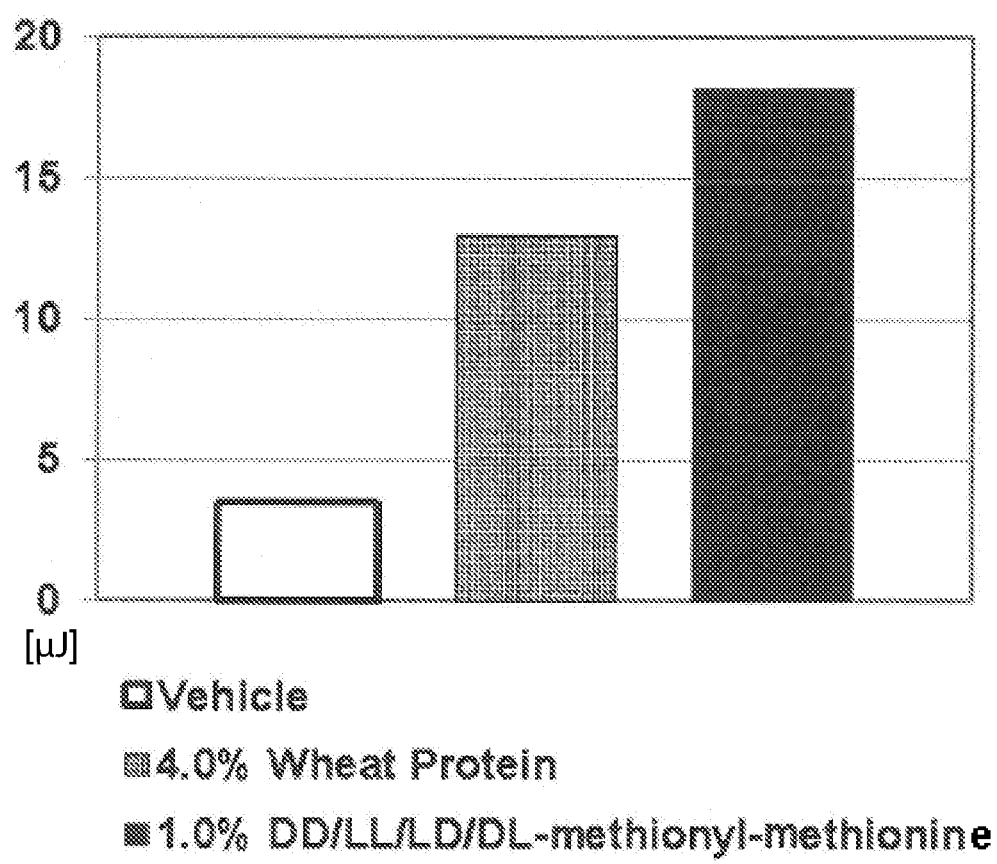
FIG. 6 is a graph illustrating the repair of bleached hair as described in the examples of the present invention.

FIG. 6: Repair of bleached hair. The improvements after hair treatment with an expanded hair conditioner (Table 4) of the parameter Work determined by means of a Tensile Tester up to 15% elongation are shown. Values shown are in microjoules (µJ).

Figure 7:
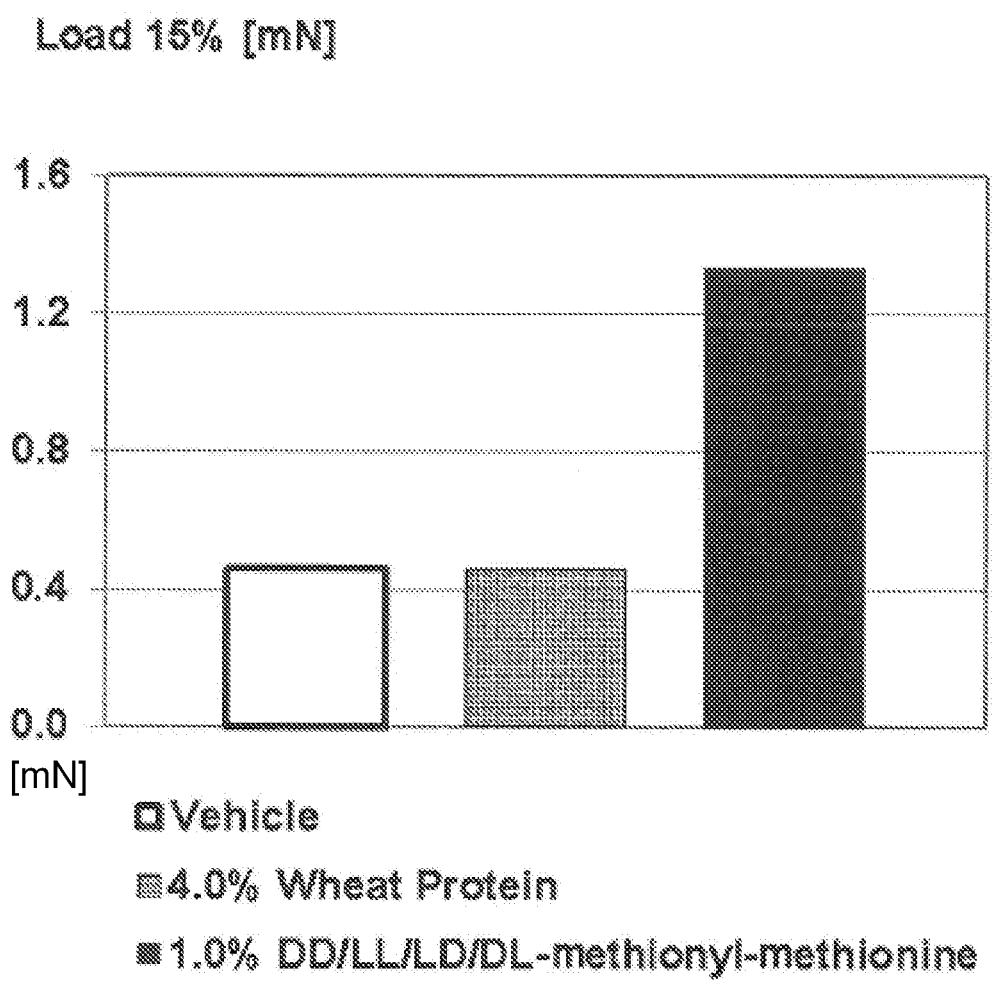
FIG. 7 is a graph illustrating the repair of bleached hair as described in the examples of the present invention.

FIG. 7: Repair of bleached hair. The improvements after hair treatment with shampoo (Table 5) of the parameter Load determined by means of a Tensile Tester at 15% elongation are shown. Values shown are in millinewtons (mN).

Figure 8:
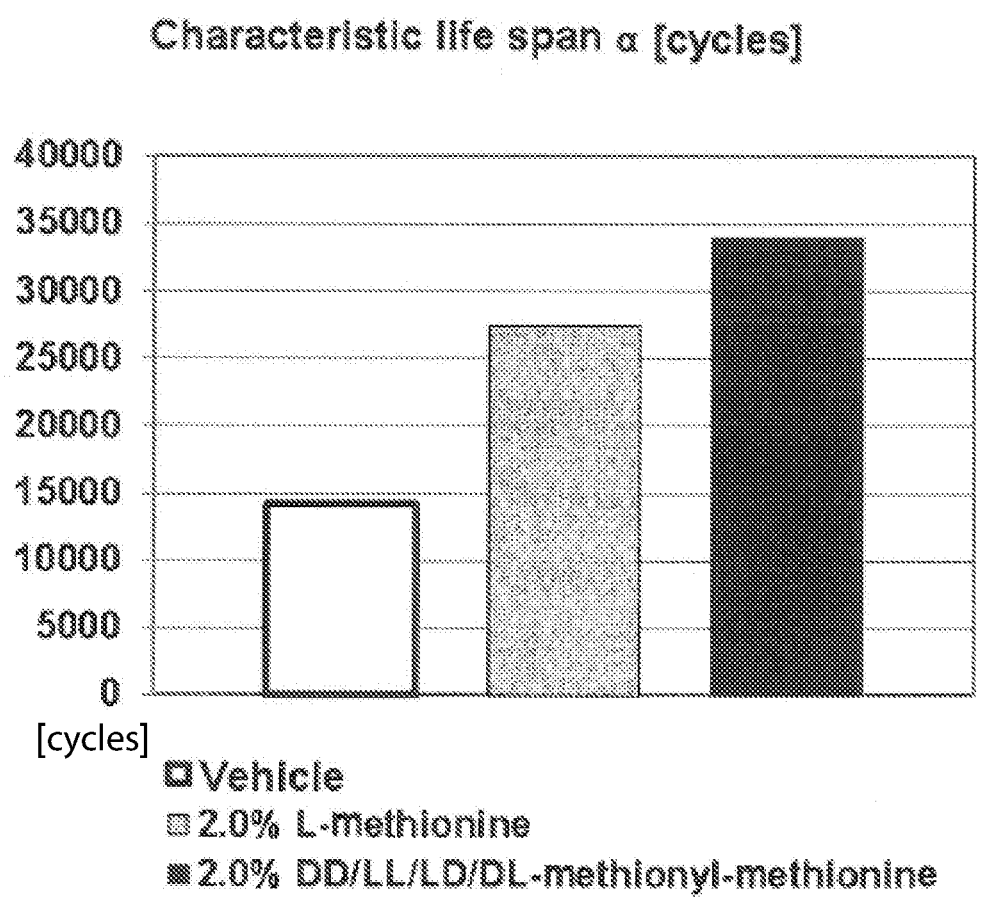
FIG. 8 is a graph illustrating the repair of bleached hair as described in the examples of the present invention.

FIG. 8: Repair of bleached hair. The characteristic life span a, determined by means of an Automatic Cyclic Tester, after hair treatment with a simple hair conditioner (Table 3) is shown. Values shown are number of cycles during which 63.2% of all hair fibres tear.

Figure 9:
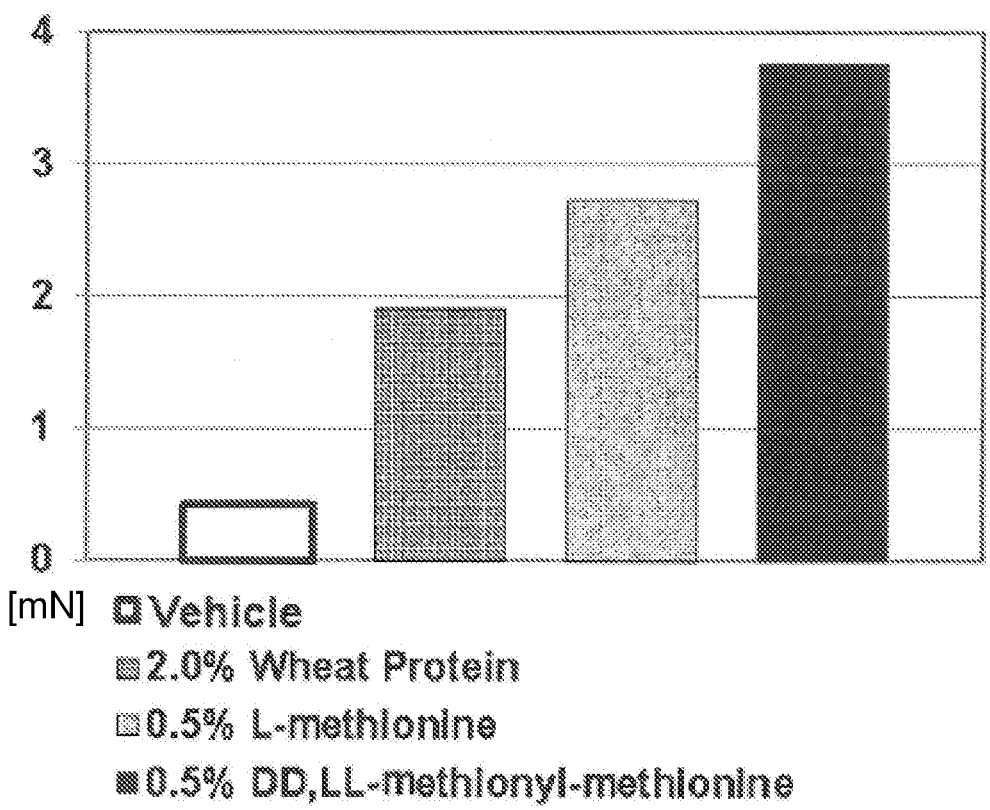
FIG. 9 is a graph illustrating the repair of alkaline smoothed hair as described in the examples of the present invention.

FIG. 9: Repair of alkaline smoothed hair. The improvements after hair treatment with a simple hair conditioner (Table 8) of the parameter Load determined by means of a Tensile Tester at 15% elongation are shown. Values shown are in millinewtons (mN).

Figure 10:
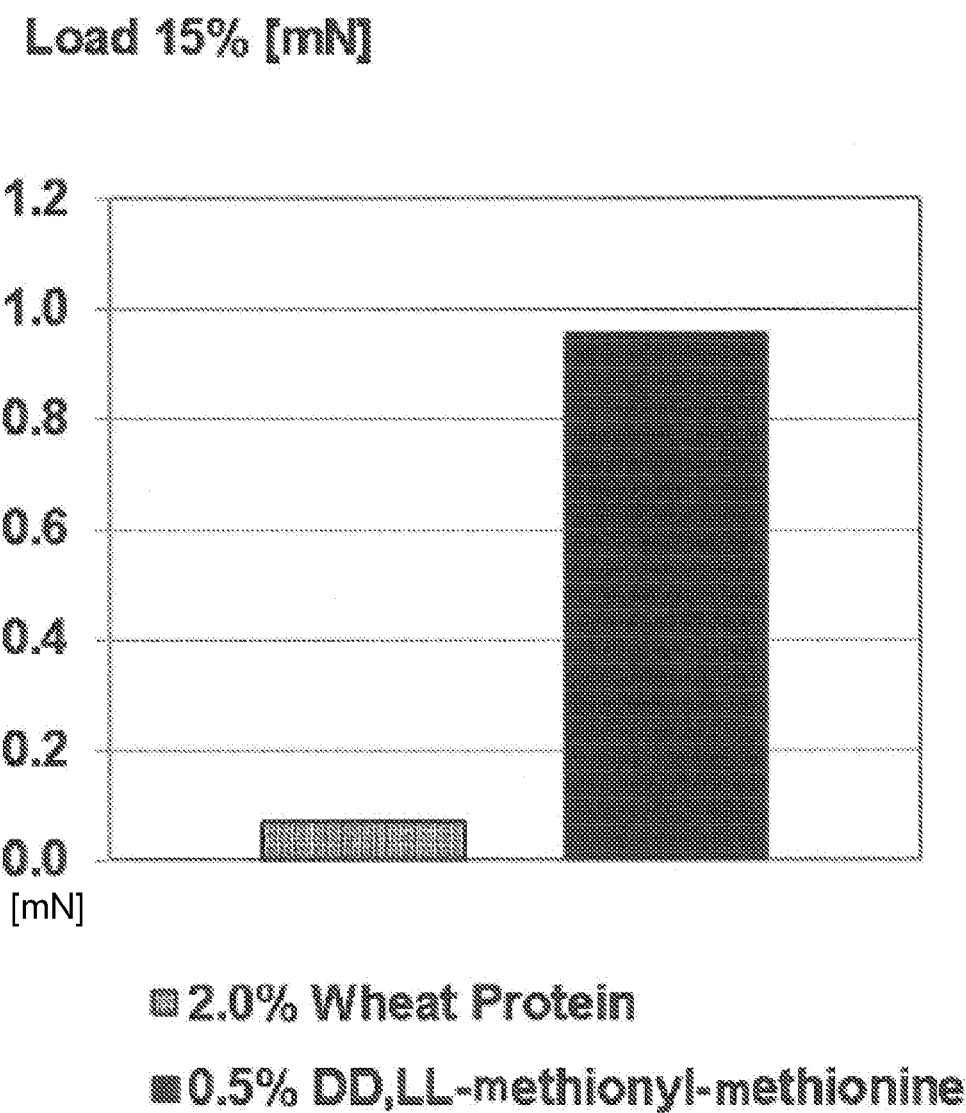
FIG. 10 is a graph illustrating the repair of reductively smoothed hair as described in the examples of the present invention.

FIG. 10: Repair of reductively smoothed hair. The improvements after hair treatment with a simple hair conditioner (Table 9) of the parameter Load determined by means of a Tensile Tester relative to vehicle at 15% elongation are shown. Values shown are in millinewtons (mN).

Figure 11:
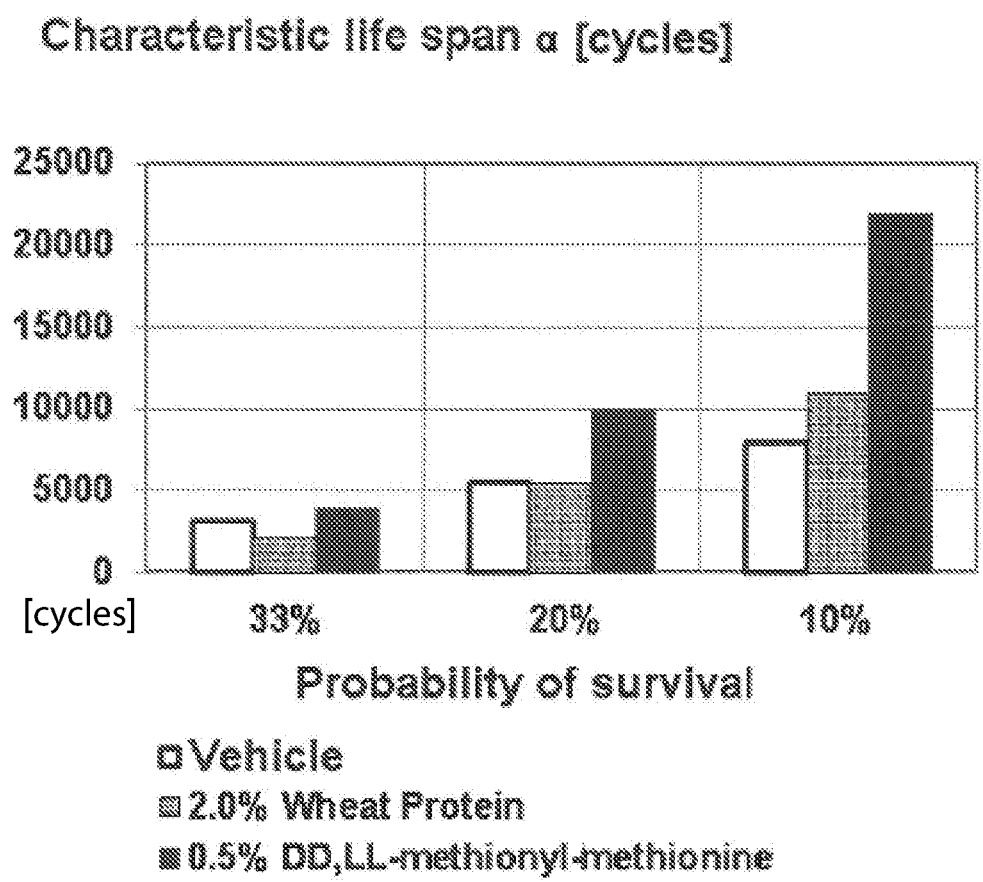
FIG. 11 is a graph illustrating the protection of the hair against thermal stress (smoothing iron treatment) by preventative treatment with active ingredient solution as described in the examples of the present invention.

FIG. 11: Protection of the hair against thermal stress (smoothing iron treatment) by preventative treatment with active ingredient solution. The characteristic life span a, determined by means of an Automatic Cyclic Tester, at 33%, 20% and 10% probability of survival is shown.

Figure 12:
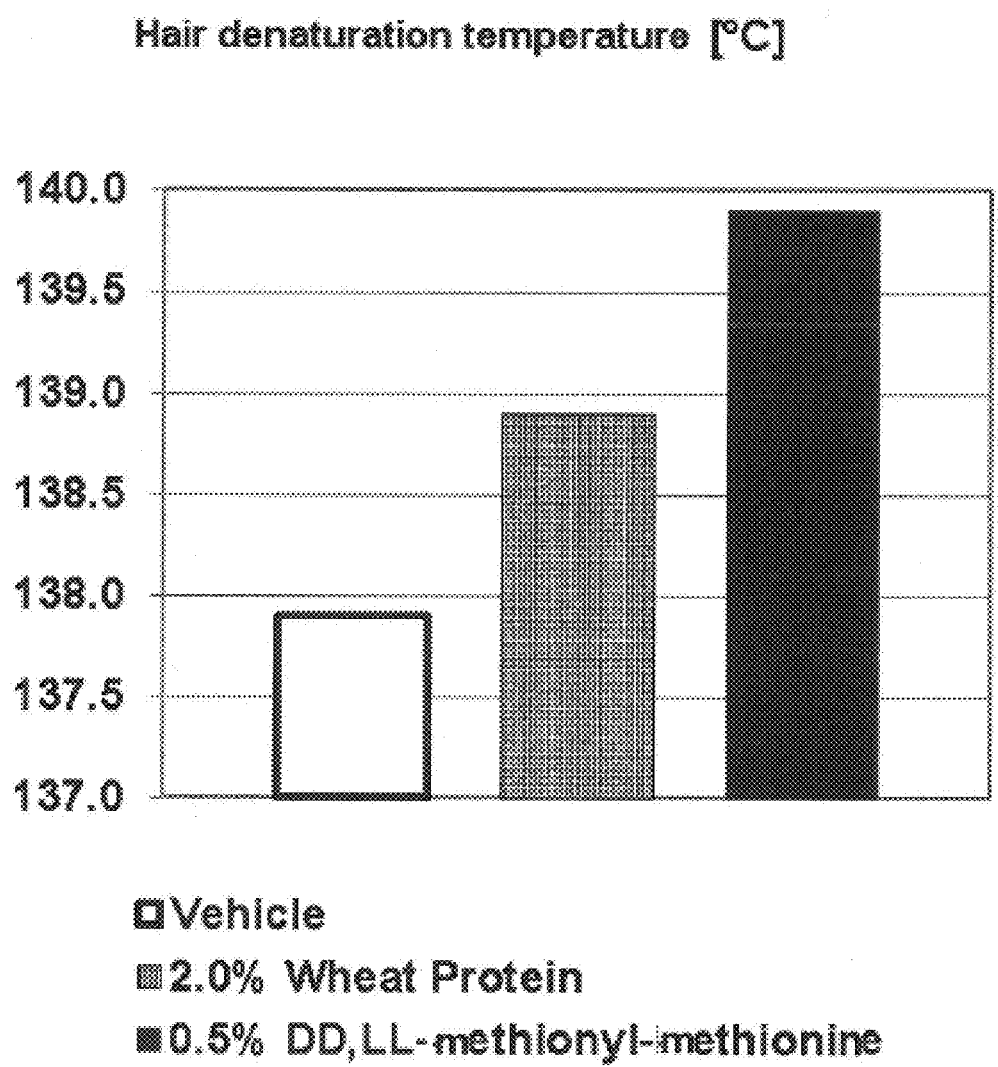
FIG. 12 is a graph illustrating the protection of the hair against thermal stress (smoothing iron treatment) by preventative protective treatment with active ingredient solution as described in the examples of the present invention.

FIG. 12: Protection of the hair against thermal stress (smoothing iron treatment) by preventative protective treatment with active ingredient solution. The improvement in the hair denaturation temperature determined by differential scanning calorimetry is shown.

EXAMPLES

Example 1

Improved Wash-Out Behavior as a Result of Treatment with Methionyl-Methionine Stereoisomers Tress sections of human Euro-Natural hair, remis, double-drawn with a length of 23 cm and a width of 2.0 cm with a weight of 2.0 g and dark-brown color were wetted under a tap of running water over the course of 10 seconds. 8 g of a 30% strength aqueous hydrogen peroxide solution were mixed with 4 g of Basler Blond Claire bleaching powder, 2 mL of a 25% strength aqueous ammonia solution were added, and combined again and 8 g of the resulting paste were massaged into the tress sections with the help of a comb and protected hands. After a contact time of 30 minutes at room temperature, the tress sections were washed for 2 minutes under running tap water at ca. 35° C. and then dried by means of an electronic hair dryer for 3 minutes while combing at the same time. The entire procedure was repeated once starting from the wetting of the tress section.

Afterwards, the tress sections were either covered with hair conditioner containing 2% LL-methionyl-methionine or with hair conditioner containing 2% DD/LL/LD/DL-methionyl-methionine (Table 1) in a plastic dish. The two different conditioning treatments were carried out in each case for a contact time of 30 minutes and of 24 hours. Then, washing was performed under a stream of running water at ca. 35° C. for 2 minutes and then drying by means of an electronic hair dryer for 3 minutes while combing at the same time.

TABLE 1

Test formulations of simple hair conditioners. Data in percent by mass. Weight ratio of DD/LL/LD/DL = 1:1:1:1. Customary formulation processes known to the person skilled in the art were used to produce the formulations.

| Raw material | LL-methionyl-methionine | DD/LL/LD/DL-methionyl-methionine |
|---|---|---|
| A TEGINACID C ® (Ceteareth-25) | 0.5% | 0.5% |
| TEGO Alkanol 1618 (Cetearyl Alcohol) | 2.0% | 2.0% |
| DD/LL/LD/DL-methionyl-methionine | | 2.0% |
| LL-methionyl-methionine | 2.0% | |
| Water | ad 100% | ad 100% |
| Preservative | q.s. | q.s. |
| Lactic acid (10% in water) | pH 4.0-4.5 | pH 4.0-4.5 |

The tress sections were halved and one part was subjected to quantitative analysis by means of HPLC in order to determine the methionyl-methionine content; the other part was firstly washed with shampoo. For the treatment with shampoo, the tress section, after drying, was wetted under a tap of running water and then 2 mL of shampoo (Table 2) were applied and massaged in by hand for ca. 2 minutes. Then, the tress section was washed under a stream of running water at ca. 35° C. for 2 minutes. The tress section was dried by means of an electronic hair dryer for 3 minutes and the shampoo treatment was repeated four times.

TABLE 2

Shampoo formulation. Data in percent by mass.
Customary formulation processes known to the person
skilled in the art were used to produce the formulations.

| | Raw material | |
|---|---|---|
| A | Texapon ® NSO (Sodium Laureth Sulfate) | 32.10% |
| | REWOMID ® C 212 (Cocamide MEA) | 1.75% |
| | TEGO ® Betain F 50 (Cocamidopropyl Betaine) | 8.00% |
| | Water | ad 100% |
| | Sodium chloride | 0.20% |
| | Preservative | q.s. |
| | Lactic acid (10% in water) | pH 5.5 |

From the treated tress sections (in each case with hair conditioner containing 2% LL-methionyl-methionine or with hair conditioner containing 2% DD/LL/LD/DL-methionyl-methionine (weight ratio of DD/LL/LD/DL=1:1:1: 1), both with and without shampoo treatment) were taken in each case ca. 100-200 mg of hair in order to determine the methionyl-methionine content. The hair sample was cut into sections 1-3 mm in length and the extraction of the methionyl-methionine was carried out in a screw-top vessel by means of duplicate extraction with an aqueous solution of 20 mM NaOH (pH~13) with vigorous shaking for 2 hours at room temperature. The extraction solutions were combined and topped up to 25 mL with 20 mM of NaOH solution. 1 mL of this was rendered neutral to acidic by adding ca. 50 µL of an aqueous solution of $H_3PO_4$ (0.2 mL 85% $H_3PO_4$ per 10 mL) and analyzed by means of HPLC.

Quantitative analysis was carried out by means of HPLC-UV on an Agilent 1100 system with Inertsil ODS-3 column (250 mm, 4.6 mm ID, 5 µm). The mobile phases used were Phase A (870 mL H2O, 5 mL MeCN, 125 mL 0.2 M H3PO4) and Phase B (400 mL H2O, 475 mL MeCN, 125 mL 0.2 M H3PO4) at 1 mL/min and 30° C. after injection of 20 µL of the analyte solution. The gradient was 10% B (0-6 min), then linear to 55% B (6-30 mM), linear back to 10% B (30-32 min) and further at 10% B (32-35 mM) Detection was carried out at 205 nm.

To produce a calibration solution, ca. 20 mg of the reference substances to be quantified were weighed into a 100 mL measuring flask and topped up to the mark with mobile phase A. The solution was treated for ca. 5 minutes in the ultrasound bath.

FIGS. 1 and 2 show in each case the results as were obtained after conditioner treatment for 30 minutes (FIG. 1) or 24 hours (FIG. 2). The remaining fraction of methionyl-methionine stereoisomers (in percent) on or in the hair after shampoo treatment had taken place, compared to non-shampooed hair, is shown.

After conditioner treatment with 2% LL-methionyl-methionine for 30 minutes, still 68.0% of the DD,LL-methionyl-methionine (sum of the enantiomer pair D-methionyl-D-methionine and L-methionyl-L-methionine) remained after shampoo treatment, whereas this fraction after conditioner treatment with 2% DD/LL/LD/DL-methionyl-methionine for 30 minutes was 80.3%. As a result of treatment with 2% DD/LL/LD/DL-methionyl-methionine for 30 minutes, following shampoo treatment additionally a further 50.0% of the DL,LD-methionyl-methionine (sum of the enantiomer pair D-methionyl-L-methionine and L-methionyl-D-methionine) were recovered. After conditioner treatment with LL-methionyl-methionine, as expected, no DL,LD-methionyl-methionine was detected following extraction of the hair.

The picture is similar following conditioner treatment for 24 hours. In the case of treatment with 2% LL-methionyl-methionine, after the shampoo treatment still 63.8% of the DD,LL-methionyl-methionine remain on or in the hair, whereas this fraction following conditioner treatment with DD/LL/LD/DL-methionyl-methionine was 66.7%. Here too, following shampoo treatment, additionally a further 68.3% of the DL,LD-methionyl-methionine were recovered.

The results of this experiment impressively demonstrate the advantages of a hair treatment with DD/LL/LD/DL-methionyl-methionine, particularly compared to a hair treatment with LL-methionyl-methionine. Firstly, it was shown that the more soluble enantiomer pair DD/LL-methionyl-methionine (21 g/L in water at room temperature), like the enantiomer-pure LL-methionyl-methionine, has a substantivity to the hair since even after a five-times shampoo treatment still clearly detectable amounts were found following extraction of the hair. The relatively recovered amounts were increased when the hair was treated with DD/LL/LD/DL-methionyl-methionine, compared to the treatment with LL-methionyl-methionine.

A yet further aspect demonstrates the advantage of a hair treatment with DD/LL/LD/DL-methionyl-methionine. Although the solubility of the enantiomer pair DL/LD-methionyl-methionine is only 0.4 g/L, surprisingly substantial amounts thereof were absorbed by the hair, and the relative recovery was still very high even after a five-times shampoo treatment. In the case of the conditioner treatment for 24 hours, the relatively recovered fraction of DL/LD-methionyl-methionine was even at its greatest, compared with the relatively recovered fraction of DD/LL-methionyl-methionine.

This unexpected, surprisingly improved substantivity clearly shows the advantage of a hair treatment with DD/LL/LD/DL-methionyl-methionine, and explains the excellent properties, indicated below, of a hair treatment with DD/LL/LD/DL-methionyl-methionine on the mechanical properties of damaged hair.

Example 2

Improvement in the Mechanical Properties of Hair Damaged by Bleach Treatment as a Result of Treatment with Methionyl-Methionine A tress section of human Euro-Natural hair, remis, double-drawn with a length of 23 cm and a width of 2.0 cm with a weight of 2.0 g and dark-brown color was wetted under a tap of running water over the course of 10 seconds. 8 g of a 30% strength aqueous hydrogen peroxide solution were mixed with 4 g of Basler Blond Claire bleaching powder, 2 mL of a 25% strength aqueous ammonia solution were added, and combined again and 8 g of the resulting paste were massaged into the tress section with the help of a comb and the protected hands. After a contact time of 30 minutes at room temperature, the tress section was washed for 2 minutes under running tap water at ca. 35° C. and then dried by means of an electronic hair dryer for 3 minutes while combing at the same time. The entire procedure was repeated once starting from the wetting of the tress section.

Afterwards, per treatment method 40 hairs were removed from the tress section and in each case the middle section of a hair with a length of 3 cm was crimped between two brass sleeves with plastic coating on the inside. The average area of each individual hair was measured using a Dia-stron FDAS760 fibre dimensional system and UvWin PC application software. The hair samples were then transferred to the sample cassette of a Dia-stron Tensile Tester MTT 670 and admixed in each case with demineralized water adjusted to pH 7 using citric acid. A measurement of the individual hair strands with the Single Fiber Method (Extension 20%, Rate 20 mm/min, Gauge Force 2, Maximum Force 200, Break Threshold 5, Sample Size 30 mm) was started. The hair samples were then removed from the sample cassette and covered with demineralized water in a plastic bowl.

For the treatment with hair conditioner, the water was removed after 30 minutes and the hair samples were covered with hair conditioner. After a contact time of 30 minutes, each individual hair sample was washed under a stream of running water at ca. 35° C. for 6 seconds. The hair samples were dried overnight at 22° C. and 50% relative atmospheric humidity.

TABLE 3

Test formulations of simple hair conditioners. Data in percent by mass. Weight ratio of DD/LL/LD/DL = 1:1:1:1. Customary formulation processes known to the person skilled in the art were used to produce the formulations.

| | Raw material | Vehicle | Wheat Protein | L-methionine | DD/LL/LD/DL-methionyl-methionine |
|---|---|---|---|---|---|
| A | TEGINACID C ® (Ceteareth-25) | 0.5% | 0.5% | 0.5% | 0.5% |
| | TEGO Alkanol 1618 (Cetearyl Alcohol) | 2.0% | 2.0% | 2.0% | 2.0% |
| | DD/LL/LD/DL-methionyl-methionine | | | | 2.0% |
| | Hydrolysed Wheat Protein (25% active substance) | | 2.0% | | |
| | L-Methionine | | | 2.0% | |
| | Water | ad 100% | ad 100% | ad 100% | ad 100% |
| | Preservative | q.s. | q.s. | q.s. | q.s. |
| | Lactic acid (10% in water) | pH 4.0-4.5 | pH 4.0-4.5 | pH 4.0-4.5 | pH 4.0-4.5 |

TABLE 4

Test formulations of expanded hair conditioners. Data in percent by mass. Weight ratio of DD/LL/LD/DL = 35:35:65:65. Customary formulation processes known to the person skilled in the art were used to produce the formulations.

| | Raw material | Vehicle | Wheat Protein | DD/LL/LD/DL-methionyl-methionine |
|---|---|---|---|---|
| A | TEGINACID C ® (Ceteareth-25) | 0.5% | 0.5% | 0.5% |
| | TEGO Alkanol 18 (Stearyl Alcohol) | 6.0% | 6.0% | 6.0% |
| | VARISOFT ® 300 (Cetrimonium Chloride) | 6.0% | 6.0% | 6.0% |
| | DD/LL/LD/DL-methionyl-methionine | | | 1.0% |
| | Hydrolysed Wheat Protein (25% active substance) | | 4.0% | |
| | Water | ad 100% | ad 100% | ad 100% |
| | Preservative | q.s. | q.s. | q.s. |
| | Lactic acid (10% in water) | pH 4.0 | pH 4.0 | pH 4.0 |

For the treatment with shampoo, the water was removed after 30 minutes and the hair samples were covered with shampoo. After a contact time of 5 minutes, each individual hair sample was washed under a stream of running water at ca. 35° C. for 6 seconds. The hair samples were briefly dried by means of an electronic hair dryer and the shampoo treatment was repeated four times.

TABLE 5

Test formulations Shampoo. Data in percent by mass. Weight ratio of DD/LL/LD/DL = 35:35:65:65. Customary formulation processes known to the person skilled in the art were used to produce the formulations.

| | Raw material | Vehicle | Wheat Protein | DD/LL/LD/DL-methionyl-methionine |
|---|---|---|---|---|
| A | Texapon ® NSO (Sodium Laureth Sulfate) | 32.10% | 32.10% | 32.10% |
| | REWOMID ® C 212 (Cocamide MEA) | 1.75% | 1.75% | 1.75% |
| | TEGO ® Betain F 50 (Cocamidopropyl Betaine) | 8.00% | 8.00% | 8.00% |
| | DD/LL/LD/DL-methionyl-methionine | | | 1.00% |
| | Hydrolyzed Wheat Protein (25% active substance) | | 4.00% | |
| | Water | ad 100% | ad 100% | ad 100% |
| | Sodium chloride | 0.20% | 0.20% | 0.20% |
| | Preservative | q.s. | q.s. | q.s. |
| | Lactic acid (10% in water) | pH 5.5 | pH 5.5 | pH 5.5 |

After the particular treatment, the measurement of the individual hair samples starting with the transfer to the sample cassette of the Dia-stron Tensile Tester MTT 670 was repeated.

The evaluation of the data takes place by reference to the parameters modulus of elasticity (E modulus), Load and/or Work. If a hair is pulled, the elongation is initially proportional to the applied force (Hooke's range). The modulus of elasticity describes the applied force per elongation (in Newton/mm$^2$) in the Hooke's range and therefore represents the tensile strength of a hair fibre. As soon as the hair has been elongated to a length of approximately 2%, it further deforms very rapidly up to ca. 25-30% of its original length, where the increase in the force required for this is minimal (Yield range). The parameter Load corresponds to the force (in Newtons) which is required to elongate the hair up to 15% and the parameter Work indicates the work required to elongate the hair from 0-15% (in Joules).

In order to measure the hair fatigue breakage, the hair samples were transferred to the sample cassette of a Diastron Automatic Cyclic Tester (CYC800) and climatized at 22° C. and 50-55% rel. atmospheric humidity. The measurement of the individual hair tresses takes place with the Constant Stress method (0.015 g/µm$^2$, max 100 000 cycles, Trigger Load 10 gmf). The characteristic life span a of a hair fibre is calculated by means of Weibull analysis. The parameter α represents the number of cycles in which 63.2% of all hair fibres tear.

As can be seen in FIGS. 3 and 4, the treatment with a simple hair conditioner already had a slight repair effect of hair damaged by bleaching, determined by measuring the tensile elongation forces by means of a Tensile Tester, at a level of 2.65 mN (Load 15%) and 11.0 µJ (Work 15%). This repair effect could be further increased neither by adding hydrolysed wheat protein nor by adding L-methionine to the hair conditioner. As a result of treatment with hair conditioner comprising DD/LL/LD/DL-methionyl-methionine, however, the value for Load 15% could be increased to 4.14 mN and for Work 15% to 19.4 µJ. Consequently, DD/LL/LD/DL-methionyl-methionine had a surprising and considerably marked repair effect on hair damaged by bleaching.

FIGS. 5 and 6 show the treatment effect of an expanded hair conditioner on hair damaged by bleaching, determined by measuring the tensile elongation forces by means of a Tensile Tester, at a level of 1.28 mN (Load 15%) and 3.51 µJ (Work 15%). This repair effect was able to be increased by adding hydrolysed wheat protein to the hair conditioner to 2.87 mN (Load 15%) and 13.0 µJ (Work 15%). As a result of treatment with hair conditioner comprising DD/LL/LD/DL-methionyl-methionine, however, the value for Load 15% was increased yet further to 4.85 mN and for Work 15% to 18.2 µJ. Consequently, treatment with DD/LL/LD/DL-methionyl-methionine had a significantly more marked repair effect on hair damaged by bleaching than treatment with hydrolyzed wheat protein.

The effect of a rinse with shampoo on hair damaged by bleaching, determined by measuring the tensile elongation forces by means of a Tensile Tester, is shown in FIG. 7. The vehicle effect had an influence on the tensile elongation forces at a level of 0.46 mN (Load 15%) and 2.46 µJ (Work 15%). This repair effect could not be increased by adding hydrolyzed wheat protein to the hair conditioner; in the case of the Work 15% parameter, a reduction in the repair effect even took place. As a result of treatment with hair conditioner comprising DD/LL/LD/DL-methionyl-methionine, however, the value for Load 15% was increased to 1.33 mN and for Work 15% slightly to 2.58 µJ. Consequently, it has been shown that treatment of hair damaged by bleaching with DD/LL/LD/DL-methionyl-methionine has a marked repair effect not only from leave-in applications, but likewise from rinse-off applications. This repair effect is noteworthy since the residence time of a shampoo on the hair is significantly shorter that the residence time of a leave-in hair conditioner and could not be attained by treatment with customary commercial active ingredients, such as for example hydrolyzed wheat protein.

FIG. 8 shows the improvement in the hair fatigue breakage of hair damaged by bleaching following treatment with a simple hair conditioner. The cycles measured by an Automatic Cyclic Tester in which 63.2% of all hair fibres tear is 14 190 after vehicle treatment. This value was increased as a result of treatment with hydrolyzed wheat protein to 27 490 cycles, but was even more marked following treatment with DD/LL/LD/DL-methionyl-methionine at a level of 33 980 cycles. DD/LL/LD/DL-methionyl-methionine thus leads to a greater reduction in hair fatigue breakage than can be attained with customary commercial standards.

In summary, it can be stated that the effect of a treatment with DD/LL/LD/DL-methionyl-methionine on hair damaged by bleaching is noticeably more marked, and unexpectedly surpasses by far the effect of a treatment with customary commercial standards.

Example 3

Improvement in the Mechanical Properties of Hair Damaged by Alkaline Smoothing Treatment as a Result of Treatment with Methionyl-Methionine A tress section of human Euro-Natural hair, remis, double-drawn with a length of 23 cm and a width of 2.0 cm with a weight of 2.0 g and dark-brown color was wetted under a tap of running water over the course of 10 seconds. 8 g of a Relaxer Cream were mixed with 2 g of Relaxer Activator and the resulting paste was applied to the tress section with the help of a brush. After a contact time of 15 minutes at room temperature, the tress section was washed for 2 minutes under running tap water at ca. 35° C. and then dried by means of an electronic hair dryer for 3 minutes while combing at the same time.

TABLE 6

Formulation Relaxer Cream. Data in percent by mass. Customary formulation processes known to the person skilled in the art were used to produce the formulations.

| | Raw material | |
|---|---|---|
| A | Water | ad 100% |
|   | TEGO ® Alkanol CS 20 P (Ceteareth-20) | 3.0% |
| B | Petrolatum | 15.0% |
|   | Mineral Oil | 10.0% |
|   | TEGO ® Alkanol 1618 (Cetearyl Alcohol) | 6.0% |
| C | Water | 10.0% |
|   | Calcium Hydroxide | 5.0% |
|   | Propylene Glycol | 2.0% |

TABLE 7

Formulation Relaxer Activator. Data in percent by mass.

| Raw material | |
|---|---|
| Water | ad 100% |
| Xanthan Gum | 0.2% |
| Guanidine Carbonate | 25.0% |
| Propylene Glycol | 2.0% |
| Preservative, perfume | q.s. |

Afterwards, 40 hairs were removed from the tress section and measured as described in Example 1. Repair treatment by means of hair conditioner and repeated measurement by means of a Dia-stron Tensile Tester MTT 670 were carried out.

TABLE 8

Test formulations of simple hair conditioners. Data in percent by mass. Weight ratio of DD/LL = 1:1. Customary formulation processes known to the person skilled in the art were used to produce the formulations.

| | Raw material | Vehicle | Wheat Protein | L-Methionine | DD/LL-methionyl-methionine |
|---|---|---|---|---|---|
| A | TEGINACID C ® (Ceteareth-25) | 0.5% | 0.5% | 0.5% | 0.5% |
| | TEGO Alkanol 1618 (Cetearyl Alcohol) | 2.0% | 2.0% | 2.0% | 2.0% |
| | DD/LL-methionyl-methionine | | | | 0.5% |
| | Hydrolysed Wheat Protein (25% active substance) | | 2.0% | | |
| | L-Methionine | | | 0.5% | |
| | Water | ad 100% | ad 100% | ad 100% | ad 100% |
| | Preservative | q.s. | q.s. | q.s. | q.s. |
| | Lactic acid (10% in water) | pH 4.0-4.5 | pH 4.0-4.5 | pH 4.0-4.5 | pH 4.0-4.5 |

FIG. 9 shows the effect of a treatment with a simple hair conditioner on hair damaged by alkaline smoothing, determined by measuring the tensile elongation forces by means of a Tensile Tester. Whereas vehicle treatment constituted only a slight repair effect at a level of 0.43 mN (Load 15%), the repair effect could be increased by adding hydrolyzed wheat protein to 1.91 mN and by adding L-methionine to 2.73 mN. By using DD/LL-methionyl-methionine, however, the value for Load 15% could be further increased to 3.76 mN.

Consequently, DD/LL-methionyl-methionine had a surprising and very marked repair effect on hair damaged by alkaline smoothing treatment, which cannot be attained to this extent with customary commercial active ingredients.

Example 4

Improvement in the Mechanical Properties of Hair Damaged by Reductive Smoothing Treatment as a Result of Treatment with Methionyl-Methionine A tress section of human Euro-Natural hair, remis, double-drawn with a length of 23 cm and a width of 2.0 cm with a weight of 2.0 g and dark-brown color was wetted under a tap of running water over the course of 10 seconds. Then, 10 g of Basler hair smoothing cream (for strong hair) were applied to the tress section with the help of a brush. During a contact time of 30 minutes at room temperature, combing was regularly carried out and then the tress section was washed for 2 minutes under running tap water at ca. 35° C. A hand towel was used to dry the hair, and Basler cream fixative (specifically for hair smoothing cream) was applied to the tress section with the help of a brush. During a contact time of 10 minutes at room temperature, combing was regularly carried out and then the tress section was washed for 2 minutes under running tap water at ca. 35° C.

Afterwards, 40 hairs were removed from the tress section and measured as described in Example 1. Repair treatment by means of hair conditioner and repeated measurement by means of a Dia-stron Tensile Tester MTT 670 were carried out.

TABLE 9

Test formulations of simple hair conditioners. Data in percent by mass. Weight ratio of DD/LL = 1:1. Customary formulation processes known to the person skilled in the art were used to produce the formulations.

| | Raw material | Vehicle | Wheat Protein | DD/LL-methionyl-methionine |
|---|---|---|---|---|
| A | TEGINACID C ® (Ceteareth-25) | 0.5% | 0.5% | 0.5% |
| | TEGO Alkanol 1618 (Cetearyl Alcohol) | 2.0% | 2.0% | 2.0% |
| | DD/LL-methionyl-methionine | | | 0.5% |
| | Hydrolyzed Wheat Protein (25% active substance) | | 2.0% | |
| | L-Methionine | | | |
| | Water | ad 100% | ad 100% | ad 100% |
| | Preservative | q.s. | q.s. | q.s. |
| | Lactic acid (10% in water) | pH 4.0-4.5 | pH 4.0-4.5 | pH 4.0-4.5 |

FIG. 10 shows the effect of a treatment with a simple hair conditioner on hair damaged by reductive smoothing, determined by measuring the tensile elongation forces by means of a Tensile Tester. Whereas treatment with hydrolyzed wheat protein constituted only a slight repair effect compared to treatment with vehicle at a level of 0.07 mN (Load 15%), the effect could be increased to 0.96 mN by using DD/LL-methionyl-methionine.

Consequently, DD/LL-methionyl-methionine had a surprising and very marked repair effect on hair damaged by reductive smoothing treatment, which cannot be attained with hydrolyzed wheat protein as customary commercial standard.

Example 5

Protection of the Hair Against Thermal Stress by Treatment with Methionyl-Methionine A tress section of human Euro-Natural hair, remis, double-drawn with a length of 23 cm and a width of 2.0 cm with a weight of 2.0 g and dark-brown color was wetted under a tap of running water over the course of 10 seconds. Then, 2 mL of shampoo (28.6% Texapon NSO in dist. water) were massaged into the hair for 30 seconds, washed out for a further 30 seconds under running tap water at ca. 35° C., and the hair tress was squeezed between two fingers and combed six times. The hair tress was dipped for 1 minute in 300 mL of active ingredient solution (active ingredient, demin. water, lactic acid, pH 5.5), squeezed between two fingers and rinsed for 30 seconds under running tap water at ca. 35° C. and combed. The hair was dried using an electronic hair dryer for 3 minutes with simultaneous combing and then stored overnight in a climatically controlled chamber (37° C., 50% rel. atmospheric humidity).

The tress section was drawn four times in each case for 30 seconds through a smoothing iron (~210° C.), which was pressed onto the tress by means of a 630 g weight. This treatment was repeated a total of five times from the wetting of the hair and shampoo treatment (in total 20 draws through the smoothing iron).

Afterwards, 50 hairs were removed from the tress section and in each case the middle section of a hair with a length of 3 cm was crimped between two brass sleeves with plastic coating on the inside. The average area of each individual hair was measured using a Dia-stron FDAS760 fibre dimensional system and UvWin PC application software.

The hair samples were then transferred to the sample cassette of a Dia-stron Automatic Cyclic Tester (CYC800) and climatized at 22° C. and 50-55% rel. atmospheric humidity. The measurement of the individual hair tresses took place with the Constant Stress method (0.015 g/µm², maximum 100 000 cycles, Trigger Load 10 gmf). The probability of survival and the characteristic life span a of a hair fibre were calculated by means of Weibull analysis.

Furthermore, hair from the tress section was chopped up using scissors and differential scanning calorimetry (Thermo Instruments Q 1000; temperature range 50-180° C.; heating rate 10° C./min) was used to determine the denaturation temperature ($T_D$).

FIG. 11 shows the protection of the hair, determined by means of hair fatigue breakage measurements, against thermal stress (smoothing iron treatment) as a result of pretreatment with active ingredient. The characteristic life span a at different probabilities of survival was given. Thus, the number of cycles at which 20% of the hair remain intact was 5500 following protective treatment with vehicle. Adding hydrolyzed wheat protein cannot increase this value, but, by using DD/LL-methionyl-methionine, DD/LL weight ratio=1:1, 20% of the hair were still intact even at 10 000 cycles. This trend was also evident for a probability of survival of 33%. The protective effect became most marked if the number of cycles was considered at which 10% of the hair did not tear. Thus, in this case the number of cycles could be increased from 8000 after vehicle treatment by using hydrolyzed wheat protein easily to 11 000, whereas the use of DD/LL-methionyl-methionine led to 10% of the hair still surviving even at 22 000 cycles.

The treatment with DD/LL-methionyl-methionine thus leads to an unexpected, impressive reduction in hair fatigue breakage, as cannot be attained with hydrolysed wheat protein as customary market standard.

FIG. 12 shows the protection of the hair, determined by differential scanning calorimetry, against thermal stress (smoothing iron treatment) as a result of pretreatment with active ingredient. The denaturation temperature in the case of vehicle-treated hair was 137.9° C. and can be increased to 138.9° C. by adding hydrolyzed wheat protein. The use of DD/LL-methionyl-methionine resulted in a further increase in the denaturation temperature to 139.9° C.

As a result of protective treatment with DD/LL-methionyl-methionine, the structure of a hair fibre can thus be greatly strengthened, which is not possible to this extent as a result of treatment with a customary market standard such as hydrolyzed wheat protein.

Example 6

Hair Tonic

|   | Raw material (INCI) | Fraction |
|---|---|---|
| A | TEGINACID ® C (Ceteareth-25) | 3.0% |
| B | Ethanol | 50.0% |
| C | DD/LL-methionyl-methionine | 0.7% |
|   | Water | ad 100% |
|   | Lactic acid (10% in water) | pH 5.5 |

Example 7

Deluxe Hair Tonic

|   | Raw material (INCI) | Fraction |
|---|---|---|
| A | TEGINACID ® C (Ceteareth-25) | 3.0% |
|   | Sphinganine | 0.2% |
| B | Ethanol | 50.0% |
| C | TEGO ® Betain C 60 (Cocamidopropyl Betaine) | 1.0% |
|   | HyaCare ® (Sodium Hyaluronate) | 0.1% |
|   | Caffeine | 1.0% |
|   | DD/LL/LD/DL-methionyl-methionine | 2.0% |
|   | Water | ad 100% |
|   | Lactic acid (10% in water) | pH 5.5 |

Example 8

Basic Leave-in Hair Conditioner Mousse

|   | Raw material (INCI) | Fraction |
|---|---|---|
| A | ABIL ® Quat 3272 (Quaternium-80) | 0.6% |
|   | TAGAT ® CH 40 (PEG-40 Hydrogenated Castor Oil) | 0.5% |
|   | Perfume | q.s. |
|   | TEGO ® Betain 810 (Capryl/Capramidopropyl Betaine) | 2.0% |
|   | Water | ad 100% |
|   | DD/LL/LD/DL-methionyl-methionine | 1.0% |
|   | TEGOCEL ® HPM 50 (Hydroxypropyl Methylcellulose) | 0.3% |
|   | VARISOFT ® 300 (Cetrimonium Chloride) | 1.3% |
|   | LACTIL ® (Sodium Lactate; Sodium PCA; Glycine; Fructose; Urea; Niacinamide; Inositol; Sodium Benzoate; Lactic Acid) | 0.5% |
|   | Citric acid, 30% | 0.1% |
|   | Preservative | q.s. |

Example 9

Special Clear Leave-in Hair Conditioner Mousse

|   | Raw material (INCI) | Fraction |
|---|---|---|
| A | ABIL ® Quat 3272 (Quaternium-80) | 0.6% |
|   | TAGAT ® CH 40 (PEG-40 Hydrogenated Castor Oil) | 0.5% |
|   | Perfume | q.s. |
|   | TEGO ® Betain 810 (Capryl/Capramidopropyl Betaine) | 2.0% |

-continued

| Raw material (INCI) | Fraction |
|---|---|
| Water | ad 100% |
| DD/LL-methionyl-methionine | 0.5% |
| TEGO ® Cosmo C 100 (Creatine) | 0.5% |
| TEGOCEL ® HPM 50 (Hydroxypropyl Methylcellulose) | 0.3% |
| VARISOFT ® 300 (Cetrimonium Chloride) | 1.3% |
| TEGO ® Natural Betaine (Betaine) | 0.5% |
| Citric acid, 30% | 0.1% |
| Preservative | q.s. |

Example 10

Hair Repair Leave-in Hair Conditioner Spray

| | Raw material (INCI) | Fraction |
|---|---|---|
| A | TAGAT ® CH 40 (PEG-40 Hydrogenated Castor Oil) | 2.00% |
| | Ceramide III (Ceramide NP) | 0.05% |
| | Perfume | q.s. |
| | Water | ad 100% |
| | ABIL ® Quat 3272 (Quaternium-80) | 0.50% |
| | ABIL ® B 88183 (PEG/PPG-20/6 Dimethicone) | 1.50% |
| | TEGO ® Smooth (Betaine; Urea; Potassium Lactate; Sodium Polyglutamate; Hydrolysed Sclerotium Gum) | 2.00% |
| | DD/LL/LD/DL-methionyl-methionine | 3.00% |
| | TEGO ® Betain F 50 (Cocamidopropyl Betaine) | 2.00% |
| | Citric acid (10% in water) | 2.00% |
| | Preservative | q.s. |

Example 11

Leave-in Hair Conditioner Mousse

| | Raw material (INCI) | Fraction |
|---|---|---|
| A | ABIL ® Quat 3272 (Quaternium-80) | 0.5% |
| | ABIL ® B 88183 (PEG/PPG-20/6 Dimethicone) | 0.4% |
| | TAGAT ® CH 40 (PEG-40 Hydrogenated Castor Oil) | 0.5% |
| | Perfume | q.s. |
| | TEGO ® Betain 810 (Capryl/Capramidopropyl Betaine) | 4.0% |
| | Water | ad 100% |
| | Panthenol | 0.2% |
| | TEGO ® Natural Betaine (Betaine) | 0.3% |
| | DD/LL/LD/DL-methionyl-methionine | 1.0% |
| | Citric acid (30% in water) | 0.4% |
| | Preservative | q.s. |

Example 12

Repair Leave-in Hair Conditioner

| | Raw material (INCI) | Fraction |
|---|---|---|
| A | TEGINACID ® C (Ceteareth-25) | 4.0% |
| | Cyclopentasiloxane; Dimethiconol | 20.0% |
| | ABIL ® Soft AF 100 (Methoxy PEG/PPG-7/3 Aminopropyl Dimethicone) | 1.0% |
| | TEGO ® Alkanol L 4 (Laureth-4) | 0.5% |
| B | TEGO ® Carbomer 140 G (Carbomer) | 0.5% |
| | Water | ad 100% |
| | 1,2-Propylene glycol (Propylene Glycol) | 5.0% |
| | DD/LL/LD/DL-methionyl-methionine | 4.0% |

-continued

| | Raw material (INCI) | Fraction |
|---|---|---|
| C | Sodium hydroxide | 0.2% |
| | Preservative, perfume | q.s. |

Example 13

Leave-in Hair Conditioner with Split-Ends Repair

| | Raw material (INCI) | Fraction |
|---|---|---|
| A | TEGINACID ® C (Ceteareth-25) | 4.0% |
| | Cyclopentasiloxane; Dimethiconol | 20.0% |
| | ABIL ® Soft AF 100 (Methoxy PEG/PPG-7/3 Aminopropyl Dimethicone) | 1.0% |
| | TEGO ® Alkanol L 4 (Laureth-4) | 0.5% |
| | VARISOFT ® BT 85 Pellets (Behentrimonium Chloride) | 0.4% |
| B | Water | ad 100% |
| | DD/LL/LD/DL-methionyl-methionine | 3.0% |
| | Propylene Glycol | 5.0% |
| | TEGO ® Carbomer 340 FD (Carbomer) | 0.5% |
| C | Sodium hydroxide (25% in water) | ad pH 5-6 |
| | Preservative, perfume | q.s. |

Example 14

Style & Relax Leave-in Hair Conditioner

| | Raw material (INCI) | Fraction |
|---|---|---|
| A | ABIL ® EM 90 (Cetyl PEG/PPG-10/1 Dimethicone) | 2.0% |
| | Paraffinum Perliquidum | 2.0% |
| | Vaseline | 2.0% |
| | ABIL ® Wax 9800 (Stearyl Dimethicone) | 2.0% |
| | Avocado (Persea Gratissima) Oil | 2.0% |
| | Olive (Olea Europaea) Oil | 2.0% |
| | TEGOSOFT ® OP (Ethylhexyl Palmitate) | 3.0% |
| | TEGOSOFT ® P (Isopropyl Palmitate) | 3.0% |
| | Simmondsia Chinensis (Jojoba) Seed Oil | 2.0% |
| | Tocopheryl Acetate | 0.2% |
| B | ABIL ® Soft AF 100 (Methoxy PEG/PPG-7/3 Aminopropyl Dimethicone) | 0.5% |
| | Glycerin | 3.0% |
| | Sodium chloride | 0.7% |
| | Water | ad 100% |
| | DD/LL-methionyl-methionine | 1.5% |
| C | Preservative, perfume | q.s. |

Example 15

"HPP" Clear Leave-in Hair Conditioner Mousse

| | Raw material (INCI) | Fraction |
|---|---|---|
| A | ABIL ® T Quat 60 (Silicone Quaternium-22) | 0.5% |
| | TAGAT ® CH 40 (PEG-40 Hydrogenated Castor Oil) | 0.5% |
| | Perfume | q.s. |
| | TEGO ® Betain 810 (Capryl/Capramidopropyl Betaine) | 2.0% |
| | Water | ad 100% |
| | DD/LL-methionyl-methionine | 0.5% |
| | TEGO ® Cosmo C 100 (Creatine) | 0.5% |
| | TEGOCEL ® HPM 50 (Hydroxypropyl Methylcellulose) | 0.3% |
| | VARISOFT ® 300 (Cetrimonium Chloride) | 1.3% |

| Raw material (INCI) | Fraction |
|---|---|
| LACTIL ® (Sodium Lactate; Sodium PCA; Glycine; Fructose; Urea; Niacinamide; Inositol; Sodium Benzoate; Lactic Acid) | 0.5% |
| Citric acid, 30% | 0.1% |
| Preservative | q.s. |

Example 16

Rich and Creamy Hair Conditioner

| | Raw material (INCI) | Fraction |
|---|---|---|
| A | Water | ad 100% |
| | Glycerin | 2.00% |
| | Propylene Glycol | 2.00% |
| | DD/LL/LD/DL-methionyl-methionine | 2.50% |
| | VARISOFT ® PATC (Palmitamidopropyltrimonium Chloride) | 2.00% |
| | TEGOSOFT ® liquid (Cetearyl Ethylhexanoate) | 2.00% |
| | TEGOSOFT ® HP (Isocetyl Palmitate) | 1.00% |
| | REWODERM ® LI S 80 (PEG-200 Hydrogenated Glyceryl Palmate; PEG-7 Glyceryl Cocoate) | 0.50% |
| | TEGO ® Alkanol 1618 (Cetearyl Alcohol) | 4.50% |
| | TEGOSOFT ® MM (Myristyl Myristate) | 1.50% |
| | ABIL ® B 8852 (PEG/PPG-4/12 Dimethicone) | 0.50% |
| | Tocopheryl Acetate | 0.25% |
| | Panthenol | 0.25% |
| | Water, preservative | q.s. |

Example 17

Brilliantine Cream for Short Hair

| | Raw material (INCI) | Fraction |
|---|---|---|
| A | ABIL ® EM 90 (Cetyl PEG/PPG-10/1 Dimethicone) | 2.5% |
| | Paraffinum Perliquidum | 7.0% |
| | Lunacera MWN (Microwax) | 1.5% |
| | Hydrogenated Castor Oil | 0.5% |
| | TEGOSOFT ® CT (Caprylic/Capric Triglyceride) | 6.0% |
| | Prunus Amygdalus Dulcis Oil | 0.5% |
| B | Water | ad 100% |
| | DD/LL-methionyl-methionine | 0.5% |
| | Sodium chloride | 0.5% |
| | Glycerin | 3.0% |

Example 18

Basic Hair and Body Shampoo

| | Raw material (INCI) | Fraction |
|---|---|---|
| A | REWOTERIC ® AM C (Sodium Cocoamphoacetate) | 15.00% |
| | REWOPOL ® SB F 12 P (Disodium Lauryl Sulfosuccinate) | 3.80% |
| | ANTIL ® Soft SC (Sorbitan Sesquicaprylate) | 0.90% |
| | Perfume | q.s. |
| | Water | ad 100% |
| | DD/LL/LD/DL-methionyl-methionine | 0.70% |
| | TEGO ® Betain F 50 (Cocamidopropyl Betaine) | 13.00% |
| | Citric acid (30% in water) | 3.00% |
| | Preservative | q.s. |

Example 19

Hair Conditioner Shampoo PEG- and Sulfate-Free

| | Raw material (INCI) | Fraction |
|---|---|---|
| A | REWOTERIC ® AM C (Sodium Cocoamphoacetate) | 15.0% |
| | REWOPOL ® SB F 12 P (Disodium Lauryl Sulfosuccinate) | 3.8% |
| | Water | ad 100% |
| | DD/LL/LD/DL-methionyl-methionine | 1.5% |
| | TEGO ® Betain F 50 (Cocamidopropyl Betaine) | 10.0% |
| | VARISOFT ® PATC (Palmitamidopropyltrimonium Chloride) | 2.3% |
| | REWOMID ® SPA (Isostearamide MIPA) | 1.0% |

Example 20

Clear Hair Shampoo with UV Protection Properties

| | Raw material (INCI) | Fraction |
|---|---|---|
| A | VARISOFT ® PATC (Palmitamidopropyltrimonium Chloride) | 1.0% |
| | ABIL ® UV Quat 50 (Polysilicone-19) | 1.0% |
| | Perfume | q.s. |
| | Water | ad 100% |
| | DD/LL-methionyl-methionine | 0.5% |
| | Sodium Laureth Sulfate, 28% | 32.0% |
| | TEGO ® Betain F 50 (Cocamidopropyl Betaine) | 8.0% |
| | ANTIL ® 171 (PEG-18 Glyceryl Oleate/Cocoate) | 2.0% |
| | Preservative | q.s. |

Example 21

Pearl & Protect Hair Conditioner Shampoo

| | Raw material (INCI) | Fraction |
|---|---|---|
| A | Water | ad 100% |
| | DD/LL/LD/DL-methionyl-methionine | 3.00% |
| | Polyquaternium-10 | 0.20% |
| | ABIL ® T Quat 60 (Silicone Quaternium-22) | 0.80% |
| | Sodium Laureth Sulfate, 28% | 25.00% |
| | REWOTERIC ® AM C (Sodium Cocoamphoacetate) | 8.00% |
| | REWOPOL ® SB C 55 (Disodium PEG-5 Laurylcitrate Sulfosuccinate; Capryl/Capramidopropyl Betaine) | 4.60% |
| | Citric acid (30% in water) | 1.80% |
| | ANTIL ® 120 | 0.20% |
| | VARISOFT ® PATC (Palmitamidopropyltrimonium Chloride) | 1.00% |
| | TEGO ® Pearl N 300 (Glycol Distearate; Laureth-4; Cocamidopropyl Betaine) | 2.00% |
| | Preservative, perfume | q.s. |

Example 22

Clear Hair Conditioner Shampoo with Ceramide

| | Raw material (INCI) | Fraction |
|---|---|---|
| A | Ceramide IIIB (Ceramide NP) | 0.05% |
| | Sodium Laureth Sulfate, 28% | 30.00% |
| | Perfume | q.s. |
| | ABIL ® Quat 3272 (Quaternium-80) | 0.50% |
| | Water | ad 100% |
| | DD/LL-methionyl-methionine | 0.50% |
| | TEGO ® Betain F 50 (Cocamidopropyl Betaine) | 10.00% |
| | ANTIL ® 171 (PEG-18 Glyceryl Oleate/Cocoate) | 2.00% |
| | Sodium chloride | q.s. |
| | Preservative | q.s. |

Example 23

Hair Conditioner Anti-Dandruff Shampoo

| | Raw material (INCI) | Fraction |
|---|---|---|
| A | TEGIN ® G 1100 Pellets (Glycol Distearate) | 3.0% |
| | Sodium Laureth Sulfate, 28% | 40.0% |
| B | Perfume | q.s. |
| | Zinc-Pyrion NF (48%) (Zinc Pyrithione) | 2.0% |
| | ABIL ® Quat 3272 (Quaternium-80) | 1.0% |
| C | Water | ad 100% |
| | DD/LL/LD/DL-methionyl-methionine | 2.5% |
| | TEGO ® Carbomer 341 ER (Acrylates/C10-30 Alkyl Acrylate Crosspolymer) | 0.2% |
| | Polyquaternium-10 | 0.3% |
| | Sodium hydroxide, 25% in water | 0.3% |
| D | REWOTERIC ® AM B U 185 (Undecylenamidopropyl Betaine) | 12.5% |
| | ANTIL ® SPA 80 (Isostearamide MIPA; Glyceryl Laurate) | 3.7% |
| Z | Preservative, perfume | q.s. |

Example 24

2 in 1 Shampoo

| | Raw material (INCI) | Fraction |
|---|---|---|
| A | Sodium Laureth Sulfate, 28% | 20.0% |
| | REWOPOL ® SB FA 30 B (Disodium Laureth Sulfosuccinate) | 6.0% |
| | TEGOSOFT ® LSE 65 K SOFT (Sucrose Cocoate) | 2.5% |
| | ABIL ® Quat 3272 (Quaternium-80) | 2.0% |
| | Water | ad 100% |
| | DD/LL/LD/DL-methionyl-methionine | 3.5% |
| | Ucare Polymer JR 400 (PolyquateRNium-10) | 0.1% |
| | TEGO ® Betain F 50 (Cocamidopropyl Betaine) | 7.0% |
| | VARISOFT ® PATC (Palmitamidopropyltrimonium Chloride) | 2.5% |
| | REWODERM ® LI S 80 (PEG-200 Hydrogenated Glyceryl Palmate; PEG-7 Glyceryl Cocoate) | 3.0% |
| | TEGO ® Pearl N 100 (Glycol Distearate; Stareth-4) | 2.0% |
| | Preservative, perfume | q.s. |

Example 25

Hair Conditioner Gel

| | Raw material (INCI) | Fraction |
|---|---|---|
| A | PEG-20 Glyceryl Laurate | 3.00% |
| | Perfume | q.s. |
| | ABIL ® B 88183 (PEG/PPG-20/6 Dimethicone) | 2.00% |
| B | Water | ad 100% |
| | DD/LL-methionyl-methionine | 1.50% |
| | TEGO ® Carbomer 140 G (Carbomer) | 1.50% |
| C | Sodium hydroxide (25% in water) | 2.20% |
| | Preservative | q.s. |

Example 26

Sun Protection Ringing Gel Wax with Mica

| | Raw material (INCI) | Fraction |
|---|---|---|
| A | Water | ad 100% |
| | Propylene Glycol | 2.00% |
| | Glycerin | 11.00% |
| | DD/LL-methionyl-methionine | 1.00% |
| | ABIL ® Soft AF 100 (Methoxy PEG/PPG-7/3 Aminopropyl Dimethicone) | 0.50% |
| B | TEGO ® Alkanol IC 20 (Isoceteth-20) | 14.50% |
| | ABIL ® UV Quat 50 (Polysilicone-19) | 2.00% |
| | TEGO ® Carbomer 140 G (Carbomer) | 1.50% |
| | TEGO ® Alkanol L 4 (Laureth-4) | 10.00% |
| | Paraffinum Perliquidum | 6.00% |
| | TEGOSOFT ® TN (C12-15 Alkyl Benzoate) | 6.00% |
| | Timiron Splendid Gold (Titanium Dioxide; Mica; Silica) | 0.05% |
| C | Perfume | q.s. |

Example 27

Hair Conditioner Rinse with UV Protection Properties, PEG-Free

| | Raw material (INCI) | Fraction |
|---|---|---|
| A | TEGO ® Alkanol 1618 (Cetearyl Alcohol) | 5.0% |
| | ABIL ® UV Quat 50 (Polysilicone-19) | 2.0% |
| B | Water | ad 100% |
| | Glycerin | 2.0% |
| | DD/LL/LD/DL-methionyl-methionine | 3.0% |
| | VARISOFT ® BT 85 Pellets (Behentrimonium Chloride) | 1.0% |
| C | Preservative, perfume | q.s. |

Example 28

Combi-Mix Clear Hair Conditioner Shampoo

| | Raw material (INCI) | Fraction |
|---|---|---|
| A | Sodium Laureth Sulfate, 28% | 28.0% |
| | ABIL ® Soft AF 100 (Methoxy PEG/PPG-7/3 Aminopropyl Dimethicone) | 0.4% |
| | Perfume | q.s. |

-continued

| Raw material (INCI) | Fraction |
|---|---|
| Water | ad 100% |
| DD/LL-methionyl-methionine | 0.7% |
| TEGO ® Cosmo C 100 (Creatine) | 1.0% |
| TEGO ® Betain F 50 (Cocamidopropyl Betaine) | 11.0% |
| ANTIL ® 171 (PEG-18 Glyceryl Oleate/Cocoate) | 2.0% |
| Sodium chloride | q.s. |
| Preservative | q.s. |

Example 29

Repair and Pearl Hair Conditioner Shampoo

| | Raw material (INCI) | Fraction |
|---|---|---|
| A | Water | ad 100% |
| | DD/LL/LD/DL-methionyl-methionine | 2.00% |
| | ABIL ® Quat 3272 (Quaternium-80) | 0.60% |
| | Sodium Laureth Sulfate, 28% | 30.00% |
| | REWOTERIC ® AM C (Sodium Cocoamphoacetate) | 8.00% |
| | REWOPOL ® SB CS 50 B (Disodium PEG-5 Laurylcitrate Sulfosuccinate; Sodium Laureth Sulfate) | 6.00% |
| | Citric acid (30% in water) | 1.80% |
| | ANTIL ® 120 PLUS (PEG-120 Methyl Glucose Dioleate) | 0.20% |
| | VARISOFT ® PATC (Palmitamidopropyltrimonium Chloride) | 2.50% |
| | Sodium chloride | 0.40% |
| | TEGO ® Pearl N 300 (Glycol Distearate; Laureth-4; Cocamidopropyl Betaine) | 2.00% |
| | Preservative | q.s. |

While the present invention has been particularly shown and described with respect to various embodiments thereof, it will be understood by those skilled in the art that the foregoing and other changes in forms and details may be made without departing from the spirit and scope of the present application. It is therefore intended that the present invention not be limited to the exact forms and details described and illustrated, but fall within the scope of the appended claims.

What is claimed as new is:

1. A method for treatment of human nails and hair, said method comprising applying a formulation comprising a stereoisomer of a methionyl-methionine of formula (I):

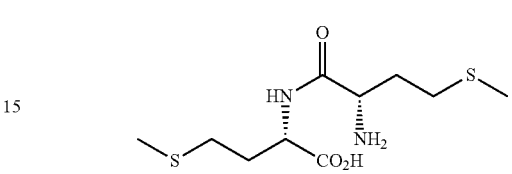

to human nails or skin.

2. The method according to claim 1, wherein said methionyl-methionine comprises at least one methionyl-methionine stereoisomer selected from the group consisting of D-methionyl-L-methionine, L-methionyl-D-methionine and D-methionyl-D-methionine.

3. The method claim 2, wherein said formulation further comprises L-methionyl-L-methionine.

4. The method according to claim 3, wherein the total amount of L-methionyl-L-methionine, based on a total weight of all methionyl-methionine stereoisomers present in the formulation, is less than 50% by weight.

5. The method according claim 3, wherein a weight ratio of DL- and LD-methionyl-methionine to DD- and LL-methionyl-methionine is from 9:1 to 2:3.

6. The method according to claim 1, wherein said formulation is a hair conditioning formulation.

* * * * *